United States Patent [19]

Brickus et al.

[11] Patent Number: 4,580,896
[45] Date of Patent: Apr. 8, 1986

[54] MULTICUVETTE CENTRIFUGAL ANALYZER ROTOR WITH ANNULAR RECESSED OPTICAL WINDOW CHANNEL

[75] Inventors: Romas A. Brickus, Brookline; Donald R. Forbush, Wollaston, both of Mass.

[73] Assignee: Allied Corporation, Morristown, N.J.

[21] Appl. No.: 549,591

[22] Filed: Nov. 7, 1983

[51] Int. Cl.[4] .............................................. G01N 1/10
[52] U.S. Cl. ..................................... 356/246; 356/244
[58] Field of Search ................................. 356/246, 244

[56] References Cited

U.S. PATENT DOCUMENTS

| | | | |
|---|---|---|---|
| Re. 31,150 | 2/1983 | Ginsberg et al. | 356/246 X |
| 3,478,598 | 11/1969 | Nielsen | 356/246 X |
| 3,586,484 | 6/1971 | Anderson | 23/230 |
| 3,759,666 | 9/1973 | Hill | 23/230 |
| 3,798,459 | 3/1974 | Anderson | 250/218 |
| 3,813,031 | 5/1974 | Anderson | 233/26 |
| 3,873,217 | 3/1975 | Anderson | 356/246 |
| 3,899,296 | 8/1975 | Mailen | 23/259 |
| 4,123,173 | 10/1978 | Bullock | 356/246 |
| 4,126,418 | 11/1978 | Krasnow | 356/246 X |
| 4,226,531 | 10/1980 | Tiffany | 356/246 |
| 4,357,301 | 11/1982 | Cassaday et al. | 356/246 X |
| 4,373,812 | 2/1983 | Stein | 356/246 |
| 4,387,992 | 6/1983 | Swartz | 356/246 |
| 4,431,606 | 2/1984 | Revillet et al. | 356/246 X |
| 4,456,581 | 1/1984 | Edelmann et al. | 356/246 X |

Primary Examiner—John E. Kittle
Assistant Examiner—Mukund J. Shah
Attorney, Agent, or Firm—Lowell H. McCarter

[57] ABSTRACT

A multicuvette rotor for use in a centrifugal analyzer includes a one piece body member of molded transparent material that defines a circumferential array of elongated cuvette recesses and a one piece cover member of molded transparent material, the cover and body member being bonded together to define a circumferential array of individually sealed separate analytical cuvettes. An annular recess in the cover member adjacent the periphery thereof has a planar optical finish base surface. Located inwardly of the annular recess in the cover member are first and second sets of circumferential arrays of loading ports so that each elongated cuvette defines a first chamber for receiving a first constituent introduced through a loading port of the first set, a second chamber region for storing a second constituent introduced through a loading port of the second set, divider structure between the first and second chamber regions that separates the two chamber regions and that has a crest portion that defines a transfer passage between the two chamber regions, and an analysis region adjacent the periphery of the cuvette where the reaction product formed by a mixture of the first and second constituents may be subjected to analysis. Structure in the base of each analytical region defines an optical window aligned with a corresponding portion of the annular recess in the cover such that an optical path for a beam of analysis radiation through the analysis region is defined.

8 Claims, 4 Drawing Figures

MULTICUVETTE CENTRIFUGAL ANALYZER ROTOR WITH ANNULAR RECESSED OPTICAL WINDOW CHANNEL

This invention relates to analysis cuvettes, and more particularly to multicuvette rotor assemblies for use in centrifugal analyzers of the photometric type.

Centrifugal analyzers are useful in performing a variety of analyses including kinetic and end point analyses. In general, such analyzers utilize a multicuvette rotor assembly which has a plurality of cuvettes that extend radially outwardly from a central hub with an annular series of inner chambers for initially holding a first group of reactants, which frequently are samples of blood or other biological fluid, an annular series of divider structures such as ramps, an annular series of outer chambers for initially holding different reactants, and an annular series of analysis regions at the periphery of the rotor. A pair of spaced optical windows in each analysis region defines an optical path of precise length along which a beam of radiation is passed for use in a photometric measurement. The rotor usually is driven at a preliminary fast speed in the vicinity of 3000-5000 rpm in which the reactant in each inner chamber flows over the divider and mixes with the reactant in the outer chamber, and then during a measurement interval the rotor is driven at speeds in the vicinity of 500-1000 rpm. The temperature of the rotor assembly during the measurement interval is closely controlled as temperature affects the reaction rates and light transmission characteristics change as the reactions proceed.

A common use of such analyzers is in the analysis of biological fluids such as blood, blood plasma or serum components, and the chemistry procedures that are performed include analyses (in an absorbance mode) for glucose, cholesterol, creatinine, total protein, calcium, phosphorous, and enzymes. Certain rotors may also be used in fluorescence and light scatter modes for analyses of glucose, bile acids, phenytoin, theophylline and gentamycin. To achieve desired analysis accuracies, the rotor must have precise and stable dimensional accuracies that are uniform between the several cuvettes of the rotor, and particularly in the analysis region between upper and lower windows at the outer end of each of the cuvettes.

Such rotors may be of the reusable type, as disclosed in Stein et al. U.S. Pat. No. 4,314,970 for example or of the disposable type as disclosed in Tiffany et al., U.S. Pat. No. 4,226,531 for example. The rotor disclosed in each of these patents has twenty cuvettes that are loaded successively with automated loading equipment, small quantities of sample (2-20 microliters) being loaded into the inner chambers and reagents in quantities of up to 200 microliters being loaded into the outer chambers. The loaded cuvette rotor is then transferred to an analyzer for photometric and/or fluorescence analysis.

Such rotors have a series of twenty individual optical windows, each of which is less than five millimeters in diameter, and each of which has a high quality optical surface finish (preferably at least three microinches). The optical windows are recessed for purposes of safeguarding their surface finishes during handling to prevent errors during analysis measurements.

Disposable rotors of the type shown in the abovementioned Tiffany patent are composed of a cover member and a body member that are permanently joined by ultrasonic welding to individually seal the twenty cuvettes. In such rotors, the twenty individual windows in the cover member are molded integrally with the cover member and are formed by highly polished mold inserts. A number of potential sources of error arise with such rotor constructions. For example, the thickness of the windows in a rotor may vary from cuvette to cuvette. The individual mold pins that define the recessed window surfaces (of about five millimeters diameter) are difficult to polish to the mirror surface finish and must be maintained with that high quality surface finish to provide the requisite optical quality window surface. Because of the small size of those mold inserts, their polished surfaces may not be precisely planar (for example edges may be rounded or nicked) or the surface may be at an angle to the axis of the insert. Also, the small molded optical areas create problems in the flow of the plastic material into those optical regions such that optical transmission distortions may result and "flash" may be formed adjacent the optical surfaces which is pulverized during the ultrasonic welding operation, creating dust which adheres to the recessed optical window surfaces and distorts the optical characteristics of the optical paths.

In accordance with the invention there is provided a multicuvette rotor for use in a centrifugal analyzer that includes a one piece body member of molded transparent material that defines a circumferential array of elongated cuvette recesses and a one piece cover member of molded transparent material, the cover and body member being bonded together to define a circumferential array of individually sealed separate analytical cuvettes. An annular recess in the cover member adjacent the periphery thereof has a planar optical finish base surface. Located inwardly of the annular recess in the cover member are first and second sets of loading ports in circumferential array so that each elongated cuvette defines a first chamber for receiving a first constituent introduced through a loading port of the first set, a second chamber region for storing a second constituent introduced through a loading port of the second set, divider structure between the first and second chamber regions that separates the two chamber regions and that has a crest portion that defines a transfer passage between the two chamber regions, and an analysis region adjacent the periphery of the cuvette where the reaction product formed by a mixture of the first and second constituents may be subjected to analysis. Structure in the base of each analytical region defines an optical window aligned with a corresponding portion of the annular recess in the cover such that an optical path for a beam of analysis radiation through the analysis region is defined.

In a particular embodiment, the annular optical window recess in the cover has an inner radius of about 4.3 centimeters, a width of about five millimeters, and its planar base surface is recessed about $\frac{1}{4}$ millimeter and has an optical finish better than three microinches. The thickness of the windows in the rotor cover do not vary from cuvette to cuvette as a ring insert in the mold defines the recessed channel window surface and is easier to polish and to maintain the required mirror surface finish to provide the requisite optical quality window surface. Because the mold insert is a single ring, its polished surface is precisely planar and defines parallel surfaces for all of the optical windows in the cover. The larger molded optical area reduces problems in the flow of the plastic material into that optical region and reduces optical transmission distortions. Also, "flash" is reduced. The annular optical window recess in the cover cooperates with the optical windows in the base to provide analysis regions at the outer ends of the reaction chamber portions of the cuvettes with optical paths of substantial effective cross sectional areas, which areas are not reduced (as was possible in the prior rotor arrangements of the type shown in the above mentioned Tiffany and Stein patents) due to misalignment of individual window regions of the cover and base members.

Other features and advantages of the invention will be seen as the following description of a particular embodiment progress, in conjunction with the drawings, in which.

DESCRIPTION OF PARTICULAR EMBODIMENT

Figure 1:
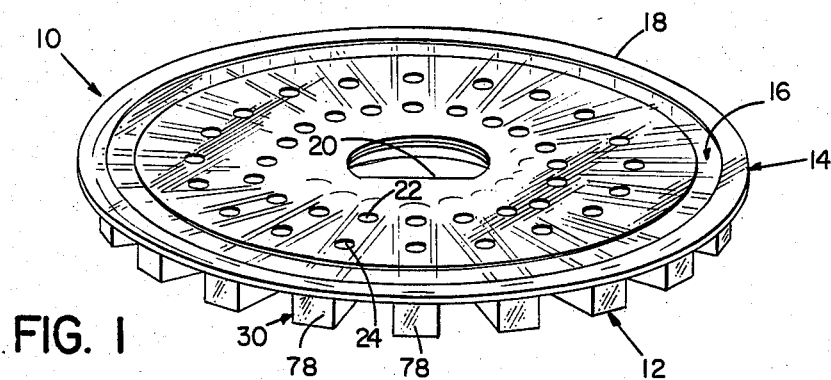
FIG. 1 is a perspective view of a multicuvette rotor assembly in accordance with the invention.
Figure 2:
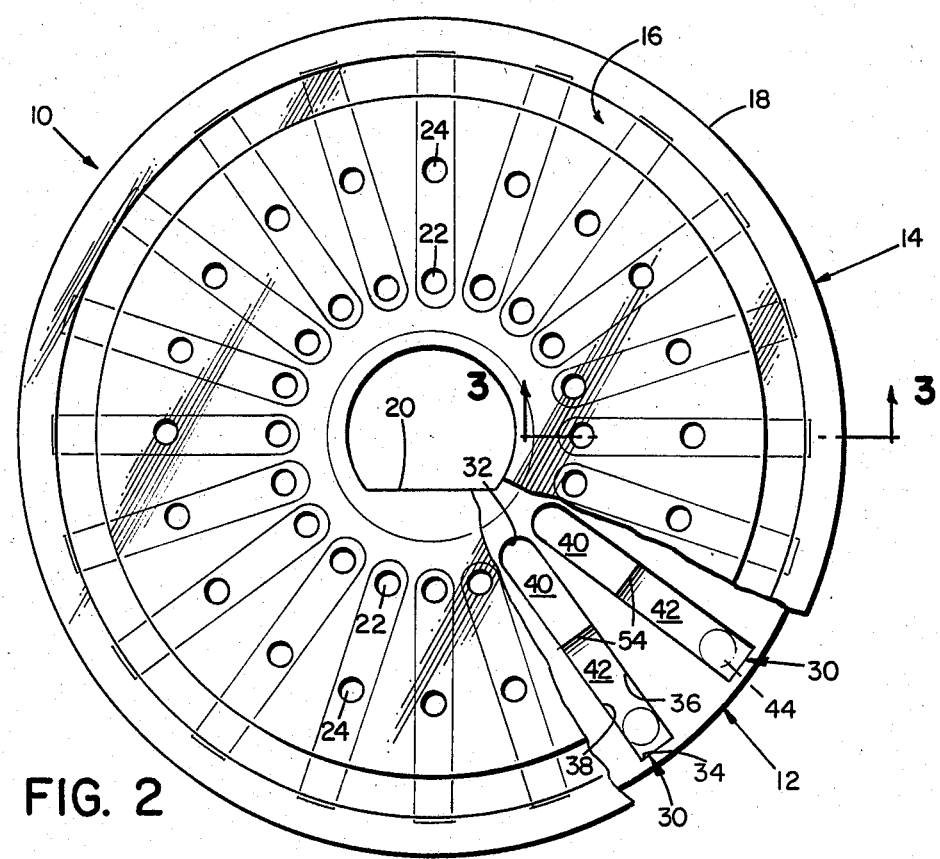
FIG. 2 is a top plan view (with portions broken away) of the multicuvette rotor assembly shown in FIG. 1.
Figure 3:
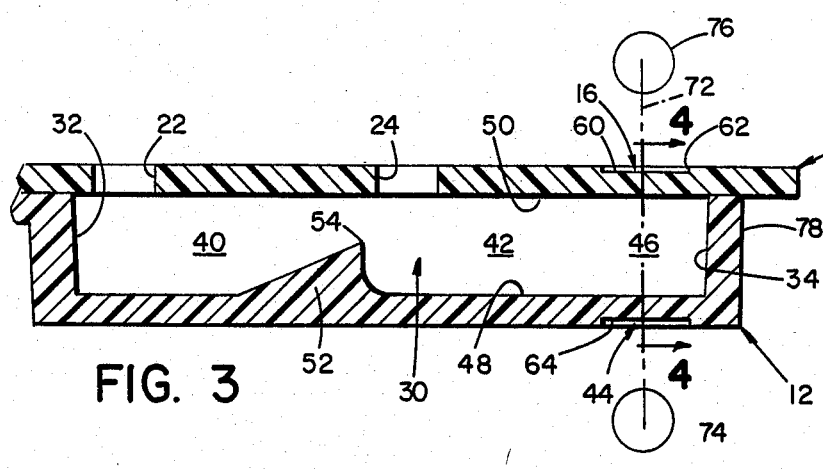
FIG. 3 is a sectional view taken along the line 3—3 of FIG. 2.
Figure 4:
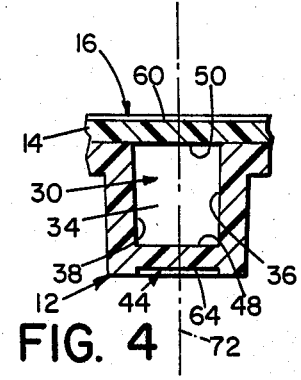
FIG. 4 is a sectional view taken along the line 4—4 of FIG. 3.

The rotor assembly 10 shown in FIG. 1 has a diameter of about ten centimeters and an overall height of about ¾ centimeter, and is formed of an injection-molded acrylic body member 12 and injection-molded acrylic cover member 14, the materials of body and cover members 12, 14 having appropriate transparency, chemical resistance, and optical characteristics for photometric analyses. Cover member 14 is a flat circular disc that has an annular recessed optical window channel 16 adjacent its peripheral edge 18, a substantially D-shaped central opening 20, a first circumferential array of loading ports 22 and a second circumferential array of loading ports 24. Body member 12 has a circumferential array of twenty individual cuvettes 30, each of which has a length of about four centimeters between a cylindrical inner wall 32 and a planar outer wall 34 that has an optical surface finish; and a width of about 0.45 centimeter between parallel planar sidewalls 36, 38. Each cuvette has an inner chamber 40 which is loaded through port 22 and an outer chamber 42 which is loaded through port 24. Formed in the base of each chamber 42 is an optical window 44 aligned with optical channel 16 to provide an analysis region 46 that has an optical path length of ½ centimeter between cuvette base surface 48 (that has an optical surface finish) and the parallel inner surface 50 of cover 14. As indicated in FIG. 3, formed in each cuvette 30 is a divider ramp structure 52 that has a radial length of about six millimeters, a crest 54 that has a height of about ¼ centimeter, an inclined planar ramp surface that forms the rear wall of cuvette chamber 40 and a planar vertical surface that forms the inner wall of cuvette chamber 42, with chamber 42 having a static capacity of about 250 microliters.

Cover member 14 is a disc that has a diameter of about ten centimeters and a thickness of about 1¼ millimeters. Channel 16 has a planar base surface 60 that is recessed about ¼ millimeter and is parallel to cover surface 50 so that an optical window of about one millimeter thickness is defined between surfaces 50 and 60. Channel 16 has a width of about ½ centimeter and its outer wall 62 is located slightly inwardly of outer wall 34 of cuvette chamber 42. Surfaces 50 and 60 both have optical finishes of better than three microinches, as do surfaces 34, 48 and 64. A similar recessed optical window 44 is formed in the base of chamber 44 between optical finish surfaces 48, 64 in alignment with channel 16 to define an analysis region through which a beam of analysis radiation may be passed along optical axis 72 between a radiation source 74 and a radiation sensor 76. The optical paths in each analysis region 46 at the outer end of each of the twenty reaction chambers 42 are of accurately defined and uniform length (between optical channel 16 and optical window 44). A similar optical window 78 is in the end wall 34 of each cuvette 30 for analyses of the fluorescence or light scattering type.

In use, the chambers 40, 42 of each cuvette 30 are loaded with appropriate reagent and sample materials in conventional manner. The loaded rotor is then placed on a rotor drive of a centrifugal analyzer. In an analysis sequence, the rotor is accelerated to about 4000 rpm during a preliminary run to flow reactant materials contained in the inner chambers 40 outwardly across ramp crests 54 into the outer chambers 42 for mixing with reactant materials in chambers 42. The rotational speed of the rotor is then reduced and successive photometric measurements are made along the optical axis 72 while the rotor 10 is being spun at rotational speeds of up to 1000 rpm.

The improved multicuvette analytical rotor assembly has uniform optical path lengths that are accurately maintained between the several cuvettes, is capable of analyzing sample volumes of 2–90 microliter size range and provides improved uniformity of clinical analyses. The thickness of the windows in the rotor cover do not vary from cuvette to cuvette as the ring insert in the mold that defines the recessed channel window surface is easier to polish and to maintain the surface finish to provide the requisite optical quality window surface. Because the mold insert is a single ring, its polished surface is precisely planar and defines parallel surfaces for all of the optical windows in the cover. Also, the larger molded optical area reduces optical transmission distortions due to flow of the plastic material into that optical region and "flash" is reduced.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. A multicuvette rotor for use in an analytical photometer, said rotor defining a circumferential array of elongated radially extending cuvettes and comprising a one-piece body member of molded transparent material that has a planar upper surface and that defines a circumferential array of elongated cuvette recesses, and a one-piece cover member of molded transparent material that has a planar lower surface parallel to the planar upper surface of said body member with a continuous seal extending around each said cuvette recess between said upper and lower surfaces to define said circumferential array of analytical cuvettes, an annular optical window recess in said cover member adjacent the periphery thereof, the base of said recess being planar and having an optical finish, said cover member having a first set of loading ports arranged in a circumferential ring and a second set of loading ports arranged in a circumferential ring, each said elongated cuvette including structure defining a first chamber for receiving a first constituent introduced through a loading port of said first set in said cover member, structure defining a second chamber region for storing a second constituent introduced through a loading port of said second set in said cover member, barrier structure between said first and second chamber regions, said barrier structure having a crest portion spaced from said lower surface of said cover member so that a transfer passage between said first and second chamber regions is defined between said crest portion and said lower surface of said cover member through which said first constituent may be flowed into said second chamber region for forming a reaction product with said second constituent, said second chamber region including an analysis region where said reaction product is subjected to analysis, and structure in the base of each said second chamber region defining an optical window aligned with a corresponding portion of said annular recess for defining a path for a beam of analysis radiation through said analysis region for analyzing the reaction product of the mixture of said first and second constituents in said analysis region.

2. The rotor of claim 1 wherein the base of said annular recess has an optical finish of at least three microinches.

3. The rotor of claim 1 wherein said annular recess has an inner radius of about four centimeters, a width of about five millimeters, and its planar base surface is recessed less than one millimeter.

4. The rotor of claim 1 wherein the optical window in the base of each said second chamber region is recessed.

5. The rotor of claim 1 and further including an optical window in the end wall of each cuvette for analyses of the fluorescence or light scattering type.

6. The rotor of claim 5 wherein each said optical window has a surface with an optical finish of at least three microinches quality.

7. The rotor of claim 6 wherein the optical window in the base of each said second chamber region is recessed about ¼ millimeter.

8. The rotor of claim 7 wherein said annular recess has an inner radius of about four centimeters, a width of about five millimeters, and its planar base surface is recessed about ¼ millimeter.

* * * * *